NECTARINE TREE
Filed Sept. 16, 1974
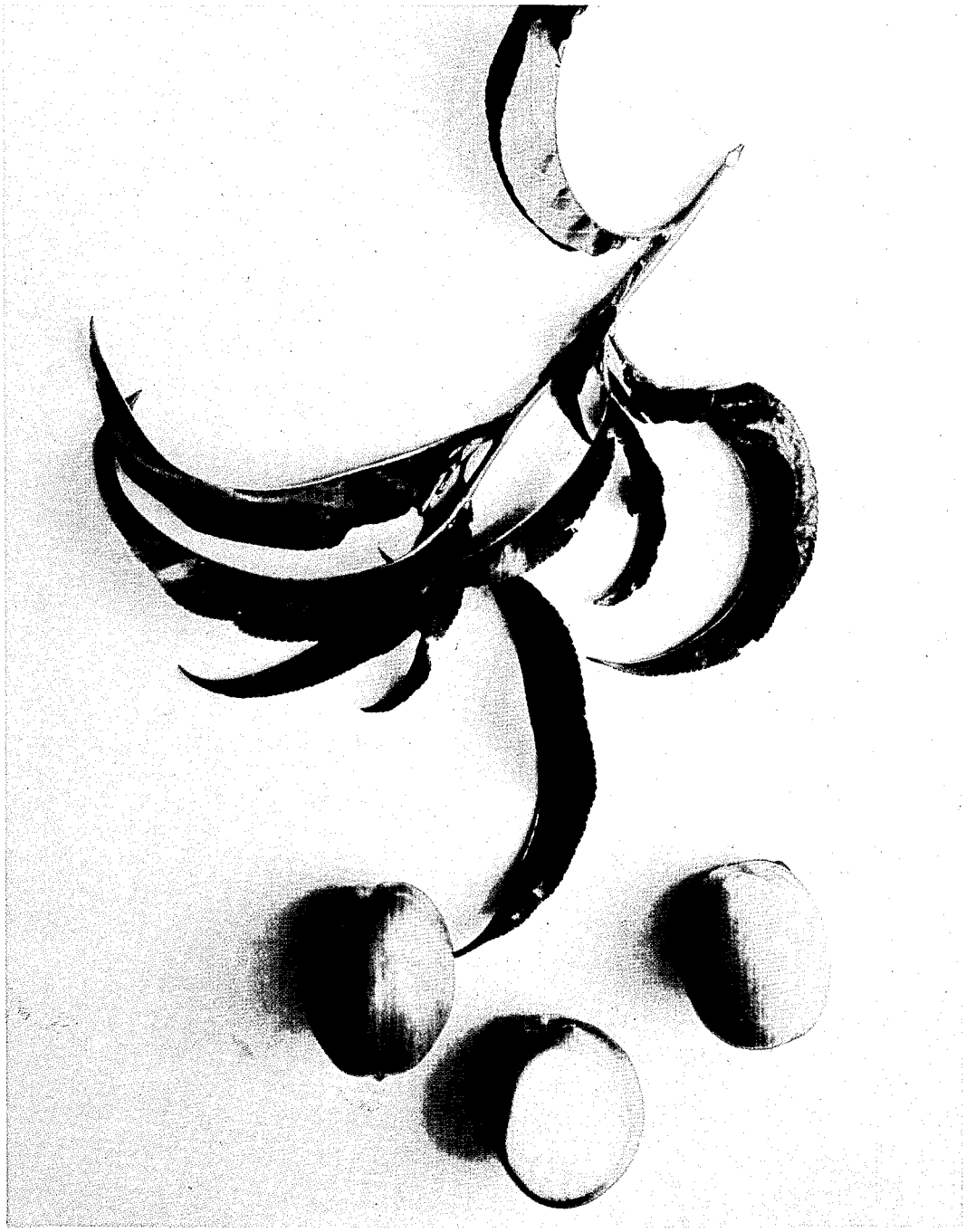

United States Patent

Plant Pat. 3,755

Patented Aug. 5, 1975

3,755

NECTARINE TREE

Frederic W. Anderson, Merced, Calif., assignor to Reedley Nursery, Inc., Reedley, Calif.

Filed Sept. 16, 1974, Ser. No. 506,731

Int. Cl. A01h *5/03*

U.S. Cl. Plt.—41 1 Claim

ABSTRACT OF THE DISCLOSURE

A nectarine tree which is of large to medium size, vigorous, upright to spreading, and foliated with medium size, lanceolate leaves having a crenate margin, and a very productive bearer of medium to small size, uniform, symmetrical, globose to oblong, clingstone fruit having firm yellow flesh and yellow skin substantially entirely overspread with a deep red. This present variety of nectarine tree is classified in Group 124 of the classification established by Caillavet and Souty in their Monographie des Principales Varietes de Pechers, 1950 edition.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present variety of nectarine tree was originated by me, in my experimental nursery and orchard, located as aforesaid, as a cross between the Red Diamond nectarine (U.S. Plant Pat. No. 3,165) as the seed parent, and the May Grand nectarine (U.S. Plant Pat. No. 2,794) as the pollen parent. The seedling resulting from such cross was grown under conditions of careful and continuing observation, and—when it bore fruit—I recognized that the variety was new and distinctive and apparently of substantial commercial promise. I, therefore, undertook asexual reproduction of the variety in anticipation of ultimate commercial growing thereof.

ASEXUAL REPRODUCTION OF THE VARIETY

The variety was successfully asexually reproduced by me in my said experimental orchard by top-working on established trees therein, and—in maturity—such reproductions ran true to the parent tree in all respects.

SUMMARY OF THE VARIETY

The present variety of nectarine tree is of large to medium size, vigorous, upright to spreading, and foliated with medium size, lanceolate leaves having a crenate margin, and a very productive bearer of medium to small size, uniform, symmetrical, globose to oblong, clingstone fruit having firm yellow flesh and yellow skin substantially entirely overspread with a deep red.

The present variety of nectarine tree is further characterized by the deep red of the skin of the fruit being—at harvest for shipment—in remarkably attractive full color much like the May Grand (the pollen parent), while the fruit has firm flesh and an unusually long shelf life similar in time-span to the Red Diamond nectarine (the seed parent). These two characteristics of the variety make possible harvesting of the fruit—for long distance shipping—when the fruit is in full color, yet with a long shelf life thereafter.

BRIEF DESCRIPTION OF THE DRAWING

The drawing is an illustration, by photographic reproduction in color, of a twig with leaves, and individual fruit, of the variety; one fruit being partially cut away to expose the flesh.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Size.*—Large to medium.
- *Vigor.*—Vigorous.
- *Growth.*—Upright to spreading.
- *Production.*—Very productive.

Trunk:
- *Size.*—Medium.

Branches:
- *Size.*—Medium.

Leaves:
- *Size.*—Medium. Average length—6½". Average width—1½".
- *Form.*—Lanceolate.
- *Thickness.*—Medium.
- *Margin.*—Crenate.
- *Petiole.*—Medium length.
- *Glands.*—Average number—3 to 4. Reniform. Usually positioned 2 on blade and 1 or 2 on petiole.
- *Color.* — Top side—Medium green (22–L–10). Under side—Lighter green (21–L–8).

Flower Buds:
- *Length.*—Medium.

Flowers:
- *Blooming period.*—About with May Grand nectarine. Medium, as compared with other varieties.
- *Size.*—Large.

Fruit:
- *Maturity when described.*—Eating ripe—June 8, 1974.
- *Date of first picking.*—May 25, 1974.
- *Date of last picking.*—June 10, 1974.
- *Size.*—Uniform. Medium to small. Average diameter axially—2¼". Average transversely in suture plane—2⅛".
- *Form.*—Uniform. Symmetrical. Globose to oblong.
- *Suture.*—Shallow. Extends from base to apex.
- *Cavity.*—Rounded.
- *Base.*—Rounded.
- *Apex.*—Short. Inconspicuous.

Skin:
- *Thickness.*—Medium.
- *Tendency to crack.*—None noted.
- *Down.*—Wanting.
- *Color.*—Yellow (11–L–8) substantially overspread with deep red (6–L–6) shading to darker red (7–L–6).

Flesh:
- *Texture.*—Firm. Crisp. Melting.
- *Ripens.*—Evenly.
- *Flavor.*—Sub-acid.
- *Eating quality.*—Good.
- *Color.*—Yellow (11–L–4). Surface of pit cavity—White to yellow.

Stone:
- *Type.*—Cling.
- *Size.*—Medium. Average length—1⅛". Average breadth—¾". Average thickness—⅝".
- *Tendency to split.*—Slight.
- *Flavor of kernel.*—Sweet.
- *Color.*—Beige (11–I–6).

Use: Market. Dessert. Long distance shipping.

Keeping quality: Good.

Resistance to insects and diseases: No unusual susceptibilities noted.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is of large to medium size, vigorous, upright to spreading, and foliated with medium size, lanceolate leaves having a crenate margin, and a very productive bearer of medium to small size, uniform, symmetrical, globose to oblong, clingstone fruit having firm yellow flesh and yellow skin substantially entirely overspread with a deep red; the deep red of the skin of the fruit being—at harvest for shipment—in remarkably attractive full color, while the fruit has firm flesh and an unusually long shelf life.

No references cited.

ROBERT E. BAGWILL, Primary Examiner